United States Patent [19]

Gumbrecht et al.

[11] Patent Number: 4,841,974
[45] Date of Patent: Jun. 27, 1989

[54] APPARATUS AND METHOD FOR THE EXAMINATION OF A LIQUID MEDIUM

[75] Inventors: Walter Gumbrecht, Erlangen; Wolfgang Schelter, Uttenreuth; Bernhard Montag, Forchheim; Peter Höbel, Buckenhof, all of Fed. Rep. of Germany

[73] Assignee: Siemens Aktiengesellschaft, Berlin and Munich, Fed. Rep. of Germany

[21] Appl. No.: 136,831

[22] Filed: Dec. 22, 1987

[30] Foreign Application Priority Data

Dec. 22, 1986 [DE] Fed. Rep. of Germany ....... 3643980

[51] Int. Cl.$^4$ .............................................. A61B 5/00
[52] U.S. Cl. ................................... 128/635; 436/68; 204/403
[58] Field of Search ................. 128/635, 632; 436/68; 204/403, 415, 416, 431, 433

[56] References Cited

U.S. PATENT DOCUMENTS

| 3,512,517 | 5/1970 | Kadish et al. ................ | 128/635 |
| 4,221,567 | 9/1980 | Clark et al. . | |
| 4,535,786 | 8/1985 | Kater . | |
| 4,592,824 | 6/1986 | Smith et al. ................ | 128/635 |
| 4,600,495 | 7/1986 | Fogt ........................... | 128/635 |

FOREIGN PATENT DOCUMENTS

| 0036171 | 9/1981 | European Pat. Off. . | |
| 0120108 | 10/1984 | European Pat. Off. . | |
| 0155725 | 9/1985 | European Pat. Off. . | |
| 0180662 | 5/1986 | European Pat. Off. ............ | 128/635 |
| 3040168 | 5/1981 | Fed. Rep. of Germany . | |
| 3038883 | 6/1984 | Fed. Rep. of Germany . | |

OTHER PUBLICATIONS

Medical and Biological Engineering Ann. N.Y. Acad. Sc., vol. 87 (1960) pp. 658–668.

Primary Examiner—Lee S. Cohen
Attorney, Agent, or Firm—Kenyon & Kenyon

[57] ABSTRACT

A measuring canal is provided which is connected to a catheter. The canal includes a measuring sensor and a reference sensor. The catheter includes several lumens that have a common opening to the liquid measuring medium. The flow direction of an infusion solution at the opening is reversible. A second lumen of the catheter is connected to the measuring canal which is provided with at least one measuring sensor and with at least one reference sensor as well as with a device for setting the outflow of the apparatus to a predetermined velocity. The flow of an infusion fluid and the liquid medium alternates in such a fashion that during a first time interval the measuring sensor is coupled to the liquid medium and the reference sensor is coupled to the infusion solution. In a second interval the situation is reversed so that the original measuring sensor is coupled to the infusion solution and the original reference sensor is connected to the liquid medium. The unique arrangement is effective for blood examination. Drift problems and toxicity problems cannot occur and no electrochemical reference electrode is required.

20 Claims, 3 Drawing Sheets

APPARATUS AND METHOD FOR THE EXAMINATION OF A LIQUID MEDIUM

BACKGROUND OF THE INVENTION

The invention relates to an apparatus for the examination of a liquid medium, especially for blood analysis in general and more particularly to an improved method and apparatus of this type.

Arrangements which include a measuring sensor which is coupled to a liquid medium to be analyzed as well as to a reference sensor and a pump, and to a liquid calibrating medium and which also include a device for measuring any differences between what is detected by the measuring sensor and what is detected by the reference sensor are known.

An electro-chemical determination of blood parameters can be substantially simultaneous to the drawing of blood from a patient who is to be monitored.

The concentrations of important blood electrolytes, such as calcium $Ca^{2+}$, potassium $K^+$, and sodium $Na^+$, or the concentration of blood gases, for instance, carbon dioxide or oxygen, or also the pH value or the presence of biomolecules such as glucose, as well as changes in these concentrations and values over time, are measured. Calcium controls various biological processes in the body, for instance, muscle contraction and the release of hormones. The clinical determination and adjustment of such concentrations can therefore be of great importance.

An ion-sensitive field effect transistor is suitable as a measuring sensor. This sensor can be integrated on a silicon chip. A control electrode serves as a membrane which forms a boundary surface to the medium to be analyzed. An electrical potential change related to the concentration to be detected is measured by a shift of ions at the boundary surface formed by the electrode. This measuring probe is known as an ISFET or ChemFET. The probe is directly connected in an alternating fashion to the medium to be analyzed, and a calibration solution. For purposes of discussion the medium to be analyzed is considered to be blood.

A valve releases either a stream of blood or the calibration solution and the released fluid flows through a heat exchanger. The heat exchanger cools the blood to room temperature. An electro-chemical reference electrode can be provided as a reference sensor. It may consist substantially of a metal electrode which is coated with a hard-to-dissolve salt of the metal. The electrode is immersed in an electrolyte solution and is closed off by a diaphragm. The reference sensor is arranged behind the ChemFET, the measuring probe, in relation to the flow direction of the blood. It can pptionally also be connected via a bridge electrolyte and a further diaphragm to the solution under analysis. While such a measuring arrangement makes possible an on-line measurement of a solution in an ex vivo arrangement of the sensor, the blood flow in the feed line hesitates during the calibration. The hesitation of the flow of the blood necessitates heparinization. In addition, the entire setup is relatively complicated. (Med. and Biol. Engineering and Computing, July 1985, pages 329 to 338).

In a further known embodiment of a measuring arrangement for blood analysis, a ChemFET is provided as a measuring sensor which is arranged at the end of a catheter at its inside wall. This measuring sensor is connected via a hose line to an electro-chemical reference electrode as well as through a reversible pump to a container that holds a calibration medium. The reference electrode is connected via a further reversible pump to an infusion solution or a flushing medium. By the pumps, in conjunction with valves, blood or the calibration medium or the flushing medium is alternatingly fed to the measuring sensor. In this embodiment, the calibration medium, as well as the flushing medium must be suitable for injection into the blood circulation of the patient. Interfering potentials can cause a polarization of the reference electrode and can thereby falsify the result of the measurement (German Patent No. 30 38 883).

It is furthermore known that in an arrangement for blood examination, a first ion-sensitive field effect transistor can be provided as the measuring sensor and another transistor can be provided as the reference sensor, between which a solution contact is arranged which is at the null potential of the measuring system. The measuring section of the device is arranged in a catheter. The measuring sensor associated with the measuring section is arranged on the outside of the catheter in the blood stream and remains in the blood track. In this arrangement, the sensor can be covered up by resting against the wall of the blood track and the function of the sensor can thereby be inhibited. Furthermore, the measuring sensor cannot be flushed, and in addition the presence of the sensor may cause a rejection reaction by the body which cannot be prevented. (European Patent OS No. 0 155 725).

A common structural unit can be formed using at least one measuring sensor, a reference sensor, and a measuring channel. Ion-selective electrodes of miniaturized design serve as sensors in the common structural unit design. The measuring channel, connected at one end to the blood stream via a catheter, is connected at the other end to a calibration solution via a reversible pump. For calibrating, the measuring channel is first filled with an infusion solution. Subsequently, blood is drawn into the measuring channel so as to bring the measuring electrode into contact with the blood and then, a different measurement is made. The blood which has been pumped into the measuring channel for the measurement is subsequently returned to the blood stream (U.S. Pat. No. 4,535,786).

In this known arrangement a solution under analysis, or also calibration solutions, which have come into contact with at least one of the sensors, are therefore returned to the patient. This means that the membranes of the sensors must therefore be sterilized. Precautions must be taken against the issuance of toxic substances from the membranes and, also against any separation or degradation of the membrane which can lead to the patient suffering health damage.

It is further known that for the determination of gases, electrolytes or sugar in the blood, a double-lumen catheter can be used. One lumen is connected to an electrode chamber. A separate calibration chamber can be connected to a reversible pump which is directly connected to the other lumen. In the catheter, there is an aperture between the two lumens. The electrode chamber contains a $CO_2$ or pH electrode, an oxygen electrode and a reference electrode. A carrier solution is pumped in a closed loop and picks up gases from the blood through a gas-permeable wall in the catheter (U.S. Pat. No. 4,221,567).

In a glucose analysis of the blood, a double-lumen needle has already been used for mixing the sample blood with heparin solution. This double channel consists of a thin plastic tube which contains a somewhat shorter inner tube, for removing the heparinized blood stream. The aperture of the inner tube is somewhat set back relative to the opening of the outer tube (Ann. N.Y. Acad. Sc., Vol. 87, (1960), pages 658 to 668).

These known measuring arrangements are complex. In addition, the liquid medium is returned to the sampling point and in some instances so is the infusion solution. This permits substances which have dissolved from membranes of the sensors to get to the sampling. Additional harm can result if the membranes are not sterilized.

SUMMARY OF THE INVENTION

The present invention obviates the above described deficiencies in known measuring arrangements. The apparatus may include:

(a) a catheter having a plurality of lumens, each of said lumens having a common opening to the liquid medium;

(b) means, coupled to a first one of said plurality of lumens, for providing a reversible flow of an infusion solution, at said opening, to and from said opening;

(c) a measuring canal coupled to a second one said plurality of lumens;

(d) means for providing an outflow through said measuring canal at a predetermined velocity;

(e) at least a first sensor and a second sensor, said measuring canal connecting said first sensor and said second sensor and, (f) wherein the size of the measuring canal is chosen so that during a first time interval said first sensor is adjacent to the infusion solution at the same time that said second sensor is adjacent to said liquid medium and during a second time interval said first sensor is adjacent to said liquid medium at the same time said second sensor is adjacent to said infusion solution;

(g) means for measuring differences between outputs of said first sensor and said second sensor.

In an embodiment of the apparatus of the present invention, an infusion solution is fed to a measuring arrangement via a catheter. The apparatus removes the necessity for a separate bridge electrolyte solution as well as an electro-chemical reference electrode with a diaphragm that is prone to contamination. All sensors of the arrangement are subjected in the time average to the same solutions; thus an ideal drift compensation is assured. Although the two sensors in this arrangement serve alternatingly as both a measuring sensor and a reference sensor, the designations measuring sensor and reference sensor are retained in the following description.

ChemFETs can preferably be provided as measuring and reference sensors. The measuring and reference sensors are provided with the same membranes. The measuring channel between the two ChemFETs can be designed with a cover strip which may act as a heat exchanger. For instance, sufficient heat transfer to the solution being analyzed can be assured by a meander-shape or serpentine shape of the measuring channel which can be preferably designed as a groove in the cover strip.

DETAILED DESCRIPTION

Figure 1:
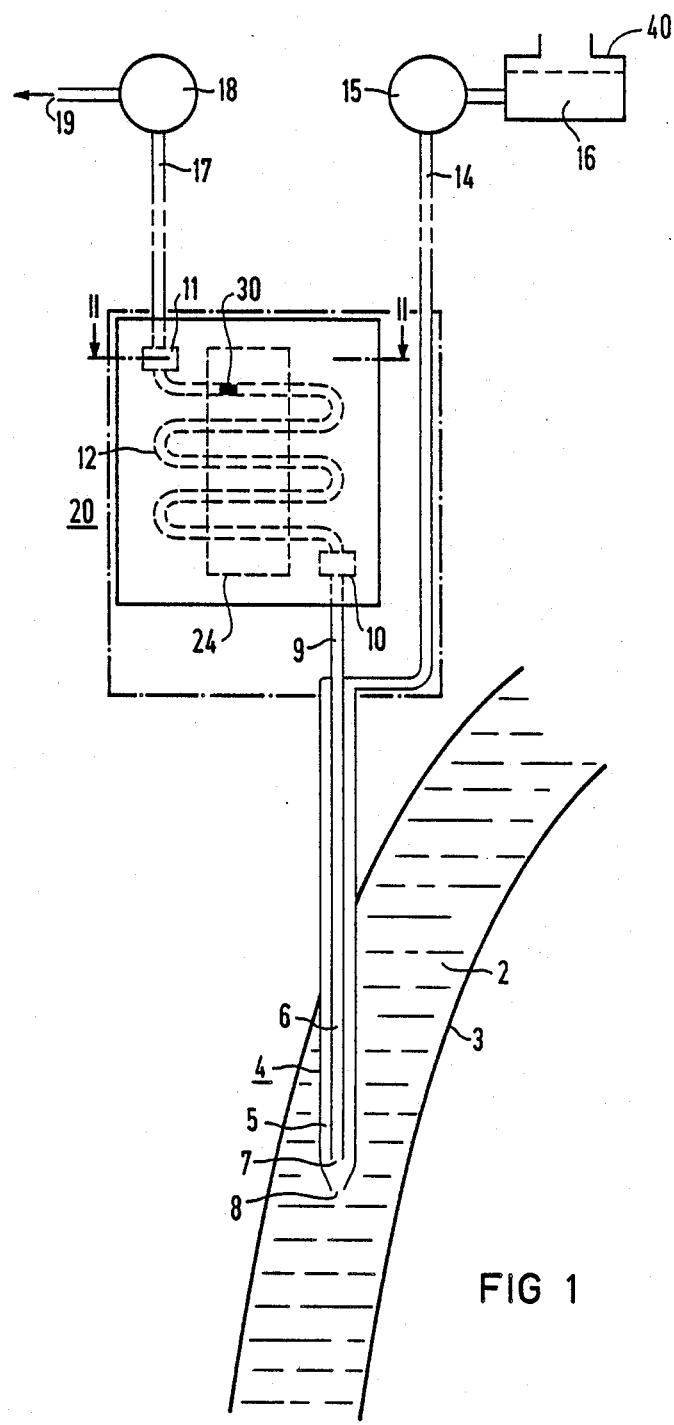
FIG. 1 shows an overall picture of measuring apparatus according to the present invention in a top view.

For purposes of explanation of the arrangement according to FIG. 1 the liquid medium is assumed to be blood.

Blood as the liquid measuring medium 2 flows through the vein 3 of a patient, not shown in the figure. A two-lumen catheter 4 with, for instance, concentrically arranged lumens is introduced into the blood stream. The outer lumen 5, is connected via an infusion hose 14 and a device for reversing the direction of flow through hose 14, such as a reversible pump 15, to a container 40 holding an infusion solution 16. The mouth 8 of the outer lumen 5 extends into the blood stream. The inner lumen 6, whose mouth 7 is located within the outer lumen 5, is connected via an infusion hose 9, a measuring channel 12 and an infusion hose 17 to a device 18 for producing a discharge of fluid at a predetermined velocity at output 19. A hose pump can preferably be used as device 18. This pump assures a constant measuring stream. A throttling valve is also suitable, for use as the device 18. The measuring channel 12 connects two sensors which are designated in the following description as the measuring sensor 10 and the reference sensor 11. Both sensors serve alternatingly as a measuring sensor as well as a reference sensor according to the arrangement of the present invention. The sensors may be ChemFETS.

Figure 2:
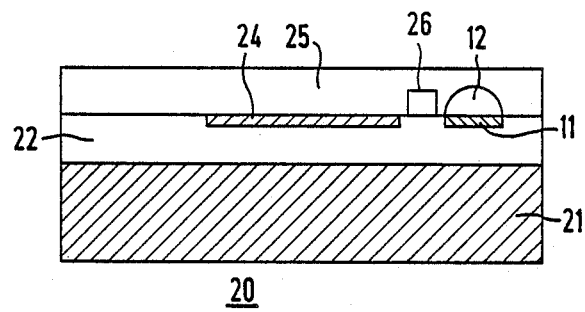
FIG. 2 illustrates a cross section of an element of the apparatus of FIG. 1.

The measuring and reference sensors 10 and 11 can preferably be integrated on a common chip 22 illustrated in FIG. 2. Evaluation electronics 24 are associated with the sensors and are disposed on the common chip 22. Optionally, a temperature sensor 26 can be associated with the common chip 22 as well, preferably forming a structural unit. The temperature sensor can be integrated on this common chip 22. Thereby, a very compact design of a sensor block 20 is obtained. The overall dimension of the block 20 does not substantially exceed about 10 mm and can be, in particular, less than 10 mm. The block 20 can preferably form a common structural unit with the catheter 4. An electrical solution contact 30 is included in the measuring arrangement. The solution contact 30 makes contact with the infusion solution 16 which serves at the same time as the reference and flushing solution. This solution contact 30 can be arranged in the flow canal 9 or the flow canal 17 or in the measuring canal 12 between the two sensors 10 and 11. Preferably the solution contact 30 is disposed in measuring canal 12 in the proximity of the reference sensor 11. The solution contact 30 electrically connects either the liquid medium to be analyzed 2 or the infusion solution 16 to the electrical reference null point of the electronic evaluation circuitry 24.

The liquid medium 2 drawn from the patient, as well as the infusion solution 16 drawn from the container 40 leave or are ejected from the measuring apparatus at the output 19.

In one embodiment of the measuring apparatus according to FIG. 1, a squeezing valve can also be provided in the catheter opening 8 for reversing a direction of flow.

According to FIG. 2, the sensor block 20 can include a base plate 21 upon Which is disposed the common chip 22 which can preferably consist of silicon. As stated above the common chip 22 may include the electronic evaluation circuitry 24 as well as measuring sensor 10 and the reference sensor 11 which are integrated circuits of the common chip 22. The sensor block 20 is covered by a cover strip 25. The measuring canal 12 may be integrated with the cover strip 25 in the form of a groove in the strip 25. The groove that forms the measuring canal 12 may have a meandering or serpentining shape.

In a special embodiment, the cover strip 25 can further include a heating device of FIG. 2. The heating device can act to thermally stabilize the liquid medium under analysis 2 and the infusion solution 16 while they are present in the measuring canal 12. For this purpose, for instance, the heating device 26 can be a semiconductor heating resistor, or a metal resistance heater. In an embodiment utilizing the heating device, the measuring arrangement is heated to the body temperature of the patient so that a numerical pH value correction becomes unnecessary, whereas such correction is necessary when the liquid medium under analysis cools off from the body temperature to the room temperature when a heating apparatus is not used. A correction that can be of an order of magnitude of the measured value may be necessary if the liquid medium is allowed to cool.

The operation of the arrangement illustrated in FIGS. 1 to 4 will now be described.

The infusion solution 16, preferably a physiological electrolyte solution and in particular, a Ringer solution, is first pumped by means of the reversible pump 15 from the container 40 through the infusion hose 14 into the outer lumen 5 of the catheter 4 toward the blood circulation of the patient. At the same time, part of this infusion solution 16 is drawn up toward the measuring sensor 10 through the opening 7 of the inner lumen 6 by the operation of device 18.

If the operation of pump 15 is reversed no longer forcing infusion solution to the opening of lumen 5, solution to be analyzed, blood, 2 is drawn through the opening 7 of the inner lumen 6 and flows into the inner lumen 6 toward sensor 10. As soon as a predetermined quantity of the solution to be analyzed 2 has flown into the inner lumen 6, the pump 15 is reversed again.

Figure 3:
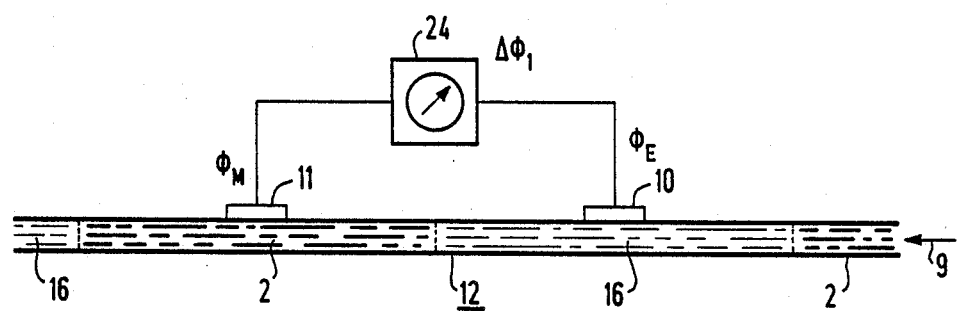
FIGS. 3 and 4 illustrate an advantageous operating method for the apparatus of FIG. 1.

In the rhythm of reversing the pump 15, a sequence of equal volumes of the liquid medium to be analyzed 2 and the infusion solution 16 are alternately drawn toward the sensors 10 and 11. The size of the volume parts of the two solutions in the measuring channel 12, dependent upon the size of the measuring channel 12, is chosen so that, as illustrated in FIG. 3, in a first time interval one sensor, for instance, the reference sensor 11 is adjacent to the infusion solution 16, while the other sensor, for instance, the measuring sensor 10 is adjacent to the solution to be analyzed 2. Similarly, in a second time interval, if the reference sensor 11 is adjacent to the solution to be analyzed 2, the measuring sensor 10 is adjacent to the infusion solution 16. In this second time interval the reference sensor 11 actually operates as a measuring sensor and the measuring sensor 10 actually operates as a reference sensor. Each sensor therefore serves alternatingly as a measuring sensor and as a reference sensor.

In a measurement With the electronic evaluation circuitry 24, which is shown for simplification in FIG. 3 as a measuring instrument, one obtains a potential difference between a measuring potential $\phi_M$ and a calibrating potential $\phi_E$ whereby:

$$\Delta\phi_1 = \phi_M - \phi_E$$

Figure 4:
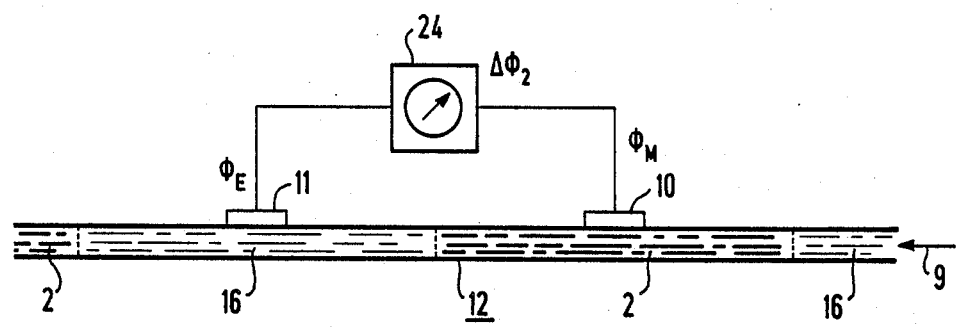

A subsequent measurement according to FIG. 4 results in a potential difference $$\Delta\phi_2 = \phi_E - \phi_M$$

In the present invention therefore $\Delta\phi_1 = \Delta\phi_2$

Figure 5:
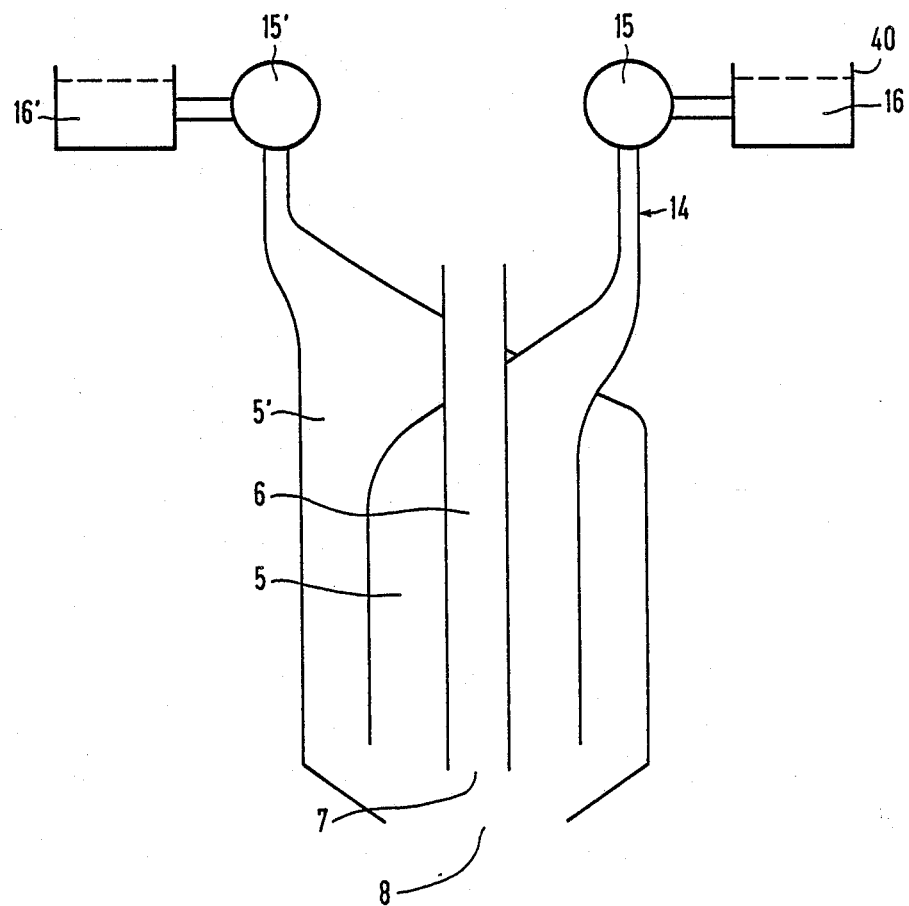
FIG. 5 illustrates an alternate embodiment for the catheter illustrated in FIG. 1.

In the embodiment illustrated in FIG. 1, a catheter is shown in which one lumen 5 is concentrically surrounded by a second lumen 6. However, it is possible to utilize two or more separate lumens arranged side by side with a common opening to the medium to be analyzed or a plurality of concentric lumens as illustrated in FIG. 5. The outer lumen can further contain additional separate lumens e.g. lumen 5' which may each be connected to different infusion solutions 16' by flow reversing means 15'. One of the lumens may be dedicated to the measurement of blood pressure.

In addition to the arrangement illustrated in FIGS. 3 and 4, it may be desirable to perform a calibration again after each measurement of the liquid medium to be analyzed. In such a case the rhythm of the reversible pump 15 is adjusted to assure that infusion solution 16 is coupled to both of the sensors 10 and 11 simultaneously after each measurement. This repetitive recalibration mode of operation reduces to one half the amount of contact over time between the sensors and the solution to be analyzed 2 compared to a system without repetitive recalibration, thus, the danger of contamination, for instance, a deposition of proteins on the membranes of the respective sensors, is accordingly slight.

As described above the arrangement of the present invention can be used for the examination of a liquid measuring medium for blood analysis. However, the arrangement can also be used advantageously in other technical fields, for instance, in biotechnology for process control, in regulation in a bioreactor, and in the continuous recording of pH values and of the concentration of harmful ions in water.

What we claim is:

1. Apparatus for the examination of a liquid medium to be analyzed, comprising:
   (a) a catheter having a plurality of lumens, each of said lumens having a common opening to the liquid medium;
   (b) means, coupled to a first one of said plurality of lumens, for providing a reversible flow of an infusion solution, at said opening, to and from said opening;
   (c) a measuring canal coupled to a second one said plurality of lumens;
   (d) means for providing an outflow through said measuring canal at a predetermined velocity;
   (e) at least a first sensor and a second sensor, said measuring canal connecting said first sensor and said second sensor;
   (f) means for measuring differences between outputs of said first sensor and said second sensor; and (g) wherein the size of the measuring canal is chosen so that during a first time interval said first sensor is adjacent to the infusion solution at the same time that said second sensor is adjacent to said liquid medium and during a second time interval said first sensor is adjacent to said liquid medium at the same time said second sensor is adjacent to said infusion solution.

2. The apparatus of claim 1, wherein said first and second sensors each comprise an ion-sensitive field effect transistor.

3. The apparatus of claim 2, wherein said field effect transistors comprise identical membranes.

4. The apparatus according to claim 1 wherein said first and said second sensors are associated with said measuring canal to form a common block.

5. The apparatus according to claim 4 wherein said first and second sensors are integrated together on a common integrated chip.

6. The apparatus according to claim 5, wherein said common integrated chip further comprises an electronic evaluation circuit connected to said first and second sensors.

7. The apparatus according to claim 5 wherein said common block further comprises a cover strip wherein said measuring canal comprises a groove in said cover strip.

8. The apparatus of claim 5, wherein said common block further comprises a means for heating said measuring canal.

9. The apparatus of claim 1 further comprising a solution contact disposed in said measuring canal between said first and second sensors.

10. The apparatus of claim 1 wherein said means for providing a reversible flow comprises a reversible pump.

11. The apparatus of claim 1 further comprising a container for the infusion solution, wherein said means for providing a reversible flow comprises a pinch valve disposed between said container for the infusion solution and the catheter.

12. The apparatus of claim 1 wherein each of said plurality of lumens beyond said first and second lumens is connected to a further infusion solution.

13. The apparatus of claim 12, wherein at least one of said plurality of lumens is provided for the measurement of blood pressure.

14. The apparatus of claim 1 further comprising a plurality of additional sensors wherein a third sensor is associated with a fourth sensor and said third and fourth sensors have identical membranes associated therewith and are connected by said measuring canal.

15. The apparatus of claim 1 further comprising a plurality of measuring sensors, and a common reference sensor wherein said common reference sensor is associated with several measuring sensors of said plurality of measuring sensors.

16. A method for examining a liquid medium, comprising the steps of:
   a. inserting a catheter, including a plurality of lumens, with a common opening, into the liquid medium;
   b. establishing a flow of liquid through a measuring channel connected to a first one of said plurality of lumens, said measuring channel including first and second sensors;
   c. feeding an infusion solution through a second one of said lumens to said common opening;
   d. periodically reversing the feeding of said infusion solution to cause alternate feeding of a first predetermined volume of the liquid medium and a second predetermined volume of infusion solution into said measuring channel;
   e. setting a rhythm of the periodic reversal to assure that during a first time interval said liquid medium is adjacent said first sensor while said infusion solution is adjacent said second sensor and during a second interval said liquid medium is adjacent said second sensor while said infusion solution is adjacent said first sensor; and
   f. measuring differences between outputs of said first sensor and said second sensor.

17. The method of claim 16 further comprising the step of:
   g. adjusting the rhythm of the periodic reversal for feeding fluids to said first lumen so that during a third time interval, between said first and second time intervals, the first and second sensors are both coupled to said infusion solution simultaneously.

18. Apparatus for the examination of a liquid medium to be analyzed, comprising:
   (a) a catheter having a plurality of lumens each of said lumens having a common opening to the liquid medium;
   (b) means, coupled to a first one of said plurality of lumens, for providing a reversible flow of an infusion solution, at said opening, to and from said opening;
   (c) measuring canal coupled to a second one of said plurality of lumens;
   (d) means for providing an outflow through said measuring canal at a predetermined velocity;
   (e) at least a first sensor and a second sensor, said measuring canal connects said first sensor to said second sensor; and
   (f) means for measuring the difference between outputs of the first sensor and the second sensor;
   (g) wherein said means for providing a reversible flow comprises a reversible pump including a means for controlling the rhythm of reversing a flow of fluid so that during a first time interval the liquid medium is adjacent the first sensor while the infusion solution is adjacent the second sensor and during a second time interval the infusion solution is adjacent the first sensor while the liquid medium is adjacent the second sensor.

19. The apparatus of claim 18, wherein each of said plurality of lumens beyond said first and second lumens is connected to a further infusion solution.

20. The apparatus of claim 19, wherein at least one of said plurality of lumens is provided for the measurement of blood pressure.

* * * * *